(12) United States Patent
Diehl et al.

(10) Patent No.: US 8,332,161 B2
(45) Date of Patent: Dec. 11, 2012

(54) METHOD FOR DETECTING A LEVEL OF CONTAMINATION OF A PARTICLE SENSOR, AND PARTICLE SENSOR

(75) Inventors: Lothar Diehl, Gerlingen (DE); Bettina Kuhn, Munich (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 291 days.

(21) Appl. No.: 12/733,955

(22) PCT Filed: Sep. 18, 2008

(86) PCT No.: PCT/EP2008/062445
§ 371 (c)(1),
(2), (4) Date: Aug. 23, 2010

(87) PCT Pub. No.: WO2009/047098
PCT Pub. Date: Apr. 16, 2009

(65) Prior Publication Data
US 2010/0312488 A1    Dec. 9, 2010

(30) Foreign Application Priority Data
Oct. 1, 2007 (DE) .................. 10 2007 047 081

(51) Int. Cl.
*G01N 25/00* (2006.01)
*G06F 19/00* (2011.01)
(52) U.S. Cl. ........................................ 702/23; 73/28.01
(58) Field of Classification Search ........... 702/23, 702/29, 32, 38, 51, 65, 81, 89, 99, 104, 106, 702/131; 73/28.01; 60/295; 123/688; 204/426; 205/784.5
See application file for complete search history.

(56) References Cited

U.S. PATENT DOCUMENTS

| | | | |
|---|---|---|---|
| 4,167,163 A | 9/1979 | Moder | |
| 8,033,159 B2 * | 10/2011 | Fleischer et al. | 73/28.01 |
| 8,182,665 B2 * | 5/2012 | Dorfmueller et al. | 204/426 |
| 2005/0279084 A1 | 12/2005 | Schmidt et al. | |
| 2009/0217737 A1 | 9/2009 | Dorfmueller et al. | |

FOREIGN PATENT DOCUMENTS

| | | |
|---|---|---|
| DE | 103 35 827 | 3/2004 |
| DE | 10 2006 002 112 | 7/2006 |
| DE | 10 2005 053 120 | 5/2007 |
| EP | 1 925 926 | 5/2008 |
| WO | WO 2005/093233 | 10/2005 |
| WO | WO 2007/000446 | 1/2007 |

* cited by examiner

*Primary Examiner* — John H Le
(74) *Attorney, Agent, or Firm* — Kenyon & Kenyon LLP

(57) ABSTRACT

In a method for detecting a level of contamination of a particle sensor provided with two electrodes situated on an insulator material for generating an electrical field, the insulator material is heated to above a limiting temperature of the insulator material at which the insulator material begins to become conductive. The insulator material is modulated by heating or cooling, the modulation being carried out at a lower temperature and an upper temperature which are each above the limiting temperature. The variation over time of a measuring signal which may be picked up between electrodes is measured during the modulation. The measured variation over time of the measuring signal is compensated using a theoretical variation over time of the measuring signal in a contamination-free state of the particle sensor in order to obtain a variation over time of a differential signal.

10 Claims, 3 Drawing Sheets

METHOD FOR DETECTING A LEVEL OF CONTAMINATION OF A PARTICLE SENSOR, AND PARTICLE SENSOR

BACKGROUND OF THE INVENTION

1. Field of the Invention

The present invention relates to a method for detecting a level of contamination of a particle sensor, and a particle sensor that is suitable therefor, with the aid of which, for example, soot particles in an exhaust gas stream of a motor vehicle may be detected.

2. Description of Related Art

A resistive particle sensor is known from published German patent application document DE 10 2005 053 120 A1 which has two comb electrodes situated on an insulator material for generating an electrical field. The particle sensor is situated in an exhaust gas stream of a motor vehicle so that soot particles may accumulate between the two electrodes. After a given time (blind period), enough soot particles have accumulated so that a current, which may be detected using a measuring device, is able to flow between the two electrodes. The measuring signal which is obtainable from the measuring device is proportional to the accumulated soot particles subsequent to a nonlinear transition phase, so that the quantity of accumulated soot particles may be detected in this linear measuring range. To prevent complete fouling of the particle sensor, the particle sensor must be regenerated by heating it to a temperature which is high enough to burn off the accumulated soot particles. The particle sensor is then ready for operation, and after the blind period has elapsed the particle sensor is able to detect accumulated soot particles.

A disadvantage of this type of particle sensor is that ash particles, which do not burn off during the regeneration of the particle sensor, also accumulate on the particle sensor.

Such ash occurs, for example, when additives are used for diesel particle filter regeneration, so that not only soot particles but also iron oxide and cerium oxide particles may accumulate in the particle sensor. The accumulated ash particles impair the accuracy of the particle sensor, so that such ash accumulations are therefore also referred to as "contamination" of the particle sensor.

BRIEF SUMMARY OF THE INVENTION

An object of the present invention is to provide a method and a particle sensor with the aid of which the contamination of the particle sensor may be detected.

In the method according to the present invention for detecting a level of contamination of a particle sensor, first a particle sensor is provided which has two electrodes situated on an insulator material for generating an electrical field. The particle sensor is situated in particular in an exhaust duct of a motor vehicle, thus enabling the particle sensor to detect soot particles contained in an exhaust gas stream of a motor vehicle. At least the insulator material of the particle sensor is heated to above a limiting temperature of the insulator material at which the insulator material begins to become conductive. This limiting temperature may be easily ascertained for any given insulator material by ascertaining a change in the ohmic resistance of the insulator material as a function of the temperature of the insulator material. Modulated heating and/or cooling of the insulator material occurs above the limiting temperature of the insulator material, the modulation taking place between a lower temperature and an upper temperature. Both the lower temperature and the upper temperature are above the limiting temperature of the insulator material. Since the insulator material is conductive at these temperatures, a measuring signal which is based, for example, on a current flow and/or a resistance measurement may be measured between the electrodes. The variation over time of the measuring signal which may be picked up between the electrodes during modulation is measured. The measured variation over time is compensated using a theoretical variation over time of the measuring signal which would be present in a contamination-free state of the particle sensor, a temperature-dependent conductivity of the insulator material being taken into account in the compensation. The theoretical variation over time of the measuring signal may be explicitly computed with knowledge of the temperature-dependent conductivity of the insulator material used, and optionally with knowledge of the thermal conductivity of the insulator material. A variation over time of a differential signal is obtained by compensating the measured variation over time using the theoretical variation over time of the measuring signal. This differential signal is evaluated to determine the level of contamination of the particle sensor. In the evaluation, the average and/or maximum signal magnitude of the differential signal is a measure of the level of contamination of the particle sensor.

In the method according to the present invention, use is made of the fact that the accumulated ash which results in contamination of the particle sensor is likewise conductive and/or becomes conductive at the modulated temperatures, and thus results in a measurable signal. However, the temperature dependency of the conductivity is a material characteristic which differs by material, so that on the basis of the temperature-dependent conductivity of the ash, which is different from that of the insulator material, a measuring signal is obtained which has a different amplitude and/or phase compared to a measurement in a contamination-free state of the particle sensor, so that a differential signal may be obtained after compensating the measured variation over time using the theoretical variation over time of a contamination-free particle sensor. The differential signal may also have undergone further processing, for example by determining the gradient of the differential signal and using same for the subsequent steps. The obtainable differential signal in particular is independent of the actual instantaneous temperature of the particle sensor, so that an accurate temperature measurement and/or knowledge of environmental parameters of the particle sensor is/are not necessary. Thus, the detection of the level of contamination of the particle sensor provides the same results when a motor vehicle in which the particle sensor is installed is being driven, as well as when the motor vehicle is idling.

The modulation is preferably carried out within a time range in which an essentially constant and/or linear measuring signal is expected during operation of the particle sensor in the absence of modulation. Superimposition of the modulation with nonlinear measurement effects is thus avoided, so that the computed compensation of the measured variation over time using the theoretical variation over time of the measuring signal is simplified.

The modulation may in particular be carried out after a regeneration period for the particle sensor and before the measurement of a changing measuring signal. Thus, the modulation may occur during the blind period of the particle sensor in which the compensation for possible interfering measuring signals is not necessary. Additionally or alternatively, the modulation may be carried out before the regeneration period for the particle sensor and within a time range in which the measuring signal changes linearly. The modulation may thus also be carried out during the customary measuring period for the particle sensor to allow contamination by accumulated ash particles to be detected, and also when accumulated soot particles are present.

During the compensation, in particular a further compensation is carried out in which a temperature-dependent conductivity of the accumulated ash and/or soot particles is taken into account. The temperature-dependent conductivity of the ash and/or soot particles may be experimentally determined. The further compensation of the variation over time of the measuring signal while additionally taking into account the temperature-dependent conductivity of the ash and/or soot particles is considered in particular in the evaluation of the differential signal, making it possible to compare the obtained differential signal with the differential signal resulting from the contamination, which may be determined by computation. This enables detection of additional shunts which are not caused by either the insulator material or by the accumulated ash and/or soot particles, and which occur, for example, via the onboard electronics system of a motor vehicle. In this manner it is possible to also detect external interferences which result in inefficient particle measurement.

A predefined tolerance band for the differential signal is preferably specified for the evaluation. Typical measuring inaccuracies may thus be taken into account. In particular, a value of the differential signal that is significantly above and/or below the tolerance band results in diagnosis of contamination of the particle sensor and/or in a correction of the measuring signal which may be picked up. The magnitude of the correction in particular is such that after the correction the differential signal is within the tolerance band. For the correction, for example, a variable electrical resistance may be set which compensates the improved conductivity via the accumulated ash.

During the compensation, it is assumed in particular that the change in the temperature-dependent conductivity is essentially linear. This simplifies the computed compensation. Since the relevant materials, in particular the insulator material, soot, and/or ash, are thermistors having a negative temperature coefficient, the conductivity, which previously was essentially constant (NTC characteristic), decreases above a certain temperature. Due to the NTC characteristic of the relevant materials, it is preferably assumed that the essentially linear change in the temperature-dependent conductivity occurs only above this temperature at which the conductivity changes, for example above the limiting temperature. Thus, the NTC characteristic may also be taken into account in the compensation.

It is particularly preferred that the heating period is longer than the cooling period during modulation. This allows the insulator material to be simultaneously heated above the limiting temperature during modulation. It is not necessary to know an instantaneous temperature of the insulator material. Instead, it may ascertained in a particularly simple manner that the limiting temperature has been exceeded to a sufficient degree when it is possible to detect a greatly changed measuring signal at both the upper temperature and the lower temperature.

It is also possible for the lower temperature and/or the upper temperature to change during modulation. This results in a differential signal with better resolution capability, since the interferences caused by the secondary flow over the accumulated particles intensify.

The present invention further relates to a particle sensor which is particularly suited for carrying out the method described above. The particle sensor has two electrodes situated on an insulator material, with the aid of which an electrical field may be generated. A measuring signal which may be picked up between the electrodes may be detected using a measuring device. In addition, a control unit is provided which, with assistance from a heating apparatus, is able to modulate a temperature of the insulator material above a limiting temperature at which the insulator material begins to become conductive, between a lower temperature and an upper temperature. The lower temperature as well as the upper temperature are above the limiting temperature. The control unit has a computing unit in which the measured variation over time of the measuring signal may be compensated using a theoretical variation over time of the measuring signal in a contamination-free state of the sensor while taking a temperature-dependent conductivity of the insulator material into account. This allows a variation over time of a differential signal to be obtained, and a level of contamination of the particle sensor may be determined based on an evaluation of the differential signal in the computing unit. As described above, the particle sensor may in particular be designed and refined using the method for detecting the level of contamination of the particle sensor.

DETAILED DESCRIPTION OF THE INVENTION

Figure 1:
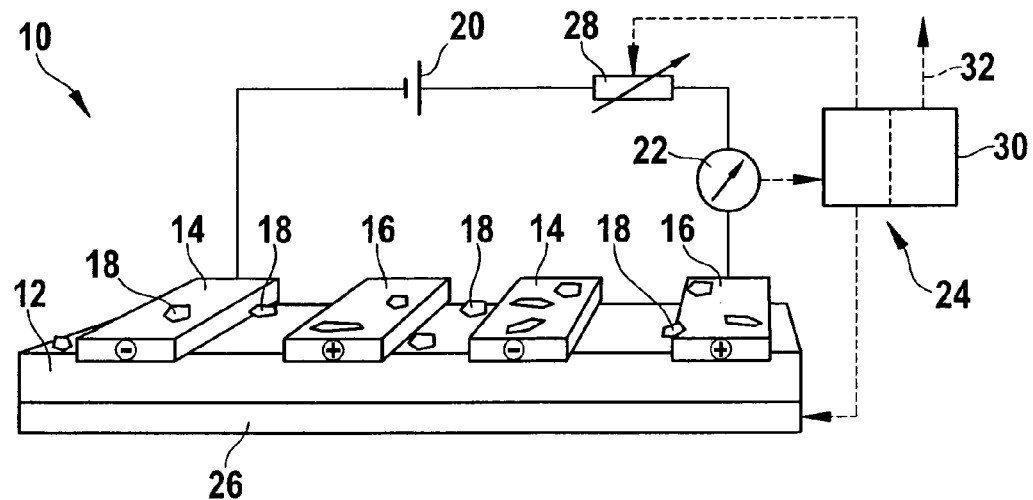
FIG. 1 shows a schematic perspective view of a particle sensor according to the present invention.

Particle sensor 10 illustrated in FIG. 1 has an insulator material 12 on which a first electrode 14 and a second electrode 16 are situated in alternation. During operation of particle sensor 10 ash particles 18 accumulate on insulator material 12 and electrodes 14, 16, which may result in an electrical shunt between first electrode 14 and second electrode 16. A power source 20 is situated between first electrode 14 and second electrode 16 for generating an electrical field between electrodes 14, 16. The resistance between electrodes 14, 16 and/or the current flowing between electrodes 14, 16 may be detected using a measuring device 22.

The variation over time of the measuring signal measured by measuring device 22 is processed in a control unit 24. Control unit 24 may also control a heating apparatus 26 in order to heat insulator material 12 above a limiting temperature at which insulator material 12 begins to become conductive, and to modulate between a lower temperature and an upper temperature, each of which are above the limiting temperature. Based on an evaluation of the obtainable measuring signal which is measured during the modulation, control unit 24 is able to vary the ohmic resistance of a variable electrical resistor 28. Control unit 24 also has a computing unit 30 in which a compensation of the measuring signal using a theoretical measuring signal as well as an evaluation of a differential signal which may be obtained via the compensation are carried out. The result of the evaluation may be relayed via a data line 32 to an onboard diagnostic unit of a motor vehicle, for example, in order to initiate measures as a function of the level of contamination of particle sensor 10.

Figure 2:
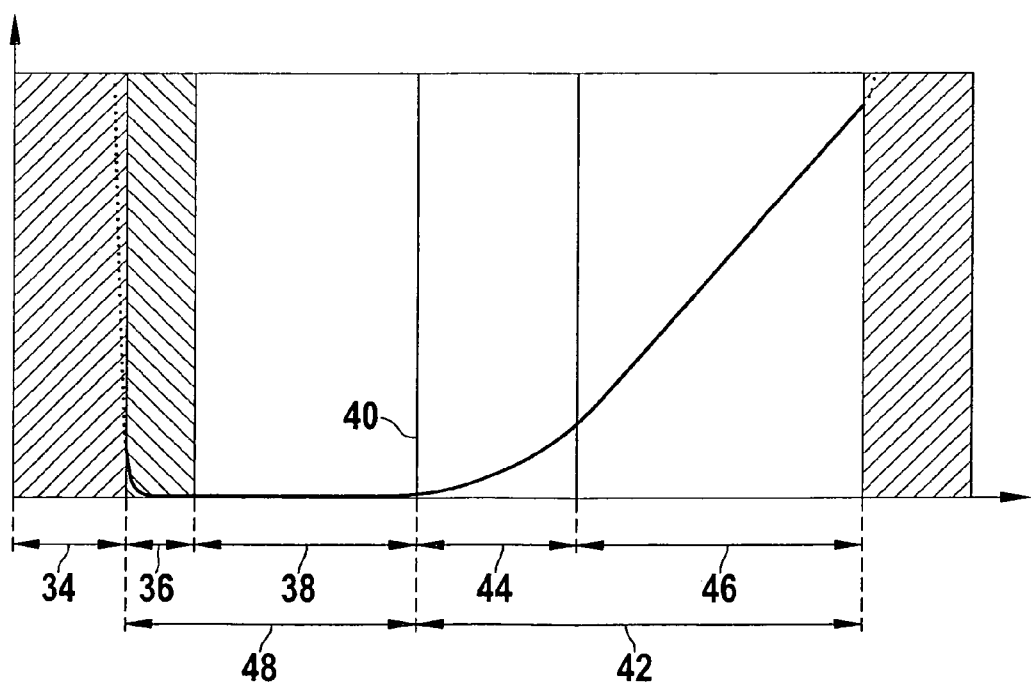
FIG. 2 shows a schematic diagram, not to scale, of a measuring signal which may be obtained from the particle sensor.

FIG. 2 illustrates as a function of time the measuring signal which is obtainable from measuring device 22 and which may be obtained during an operating cycle of particle sensor 10. Soot particles accumulated on particle sensor 10 are burned off in a regeneration phase 34. During a thermalization phase 36 the particle sensor is then brought to its customary operating temperature. This is followed by a blind period 38 in which enough soot particles are accumulated on particle sensor 10 until it is possible to detect a measuring signal at a trigger point 40 and a measuring period 42 begins, it being possible in principle to use any region for signal interpretation. Measuring period 42 has a nonlinear transition region 44 which is followed by a linear measuring range 46. As soon as excessive soot particles have accumulated on particle sensor 10, a regeneration period 34 for burning off the soot particles is carried out again, followed by a trigger period 48 until measuring period 42 begins once again.

Figure 3:
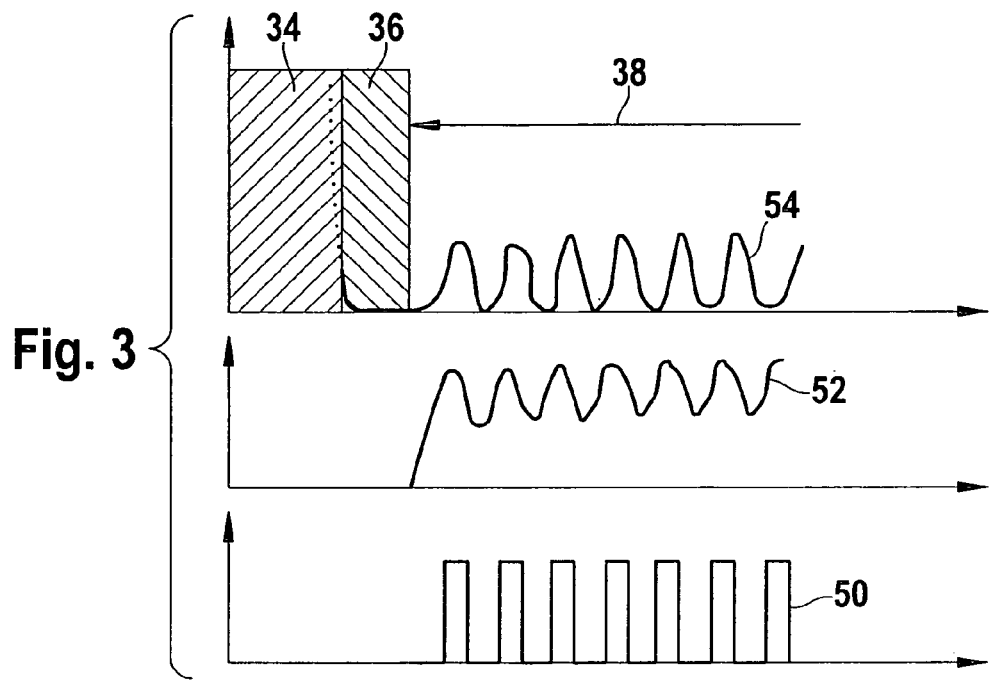
FIG. 3 shows a schematic comparison of parameters obtainable during a modulation.

As illustrated in the lower diagram in FIG. 3, heating capacity 50 of heating apparatus 26 may have a rectangular curve during a modulation in blind period 38, resulting in curve 52 of the insulator material temperature illustrated in the middle diagram. For an uncontaminated particle sensor 10, this results in measuring signal 54 during blind period 38 illustrated in the upper diagram.

Figure 4:
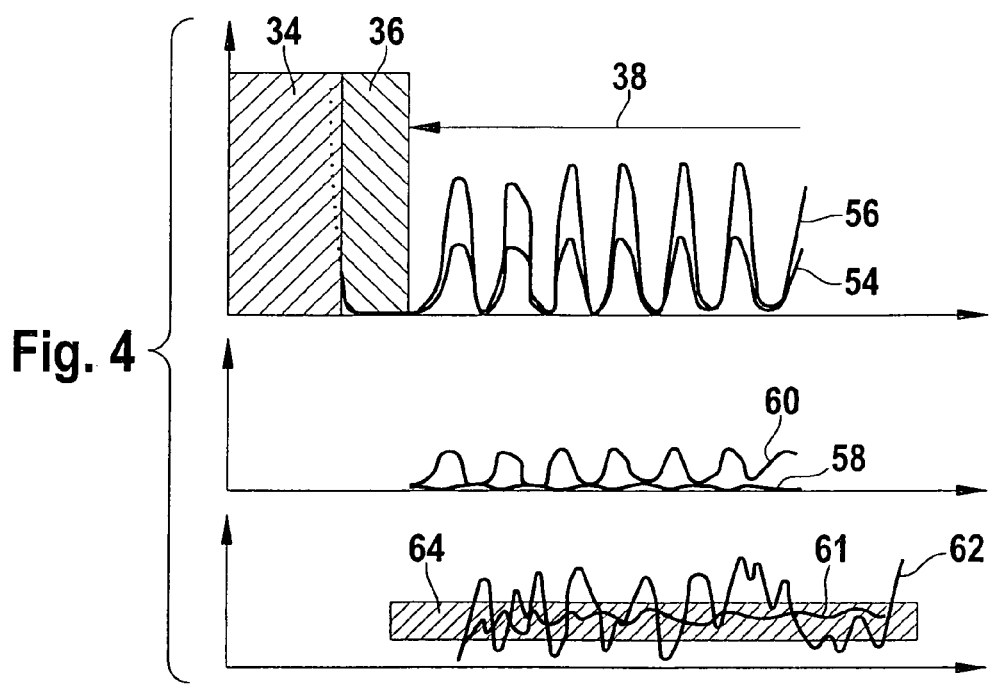
FIG. 4 shows a schematic comparison of parameters obtainable during a modulation in the contaminated and uncontaminated states of the particle sensor in a first time period.

In the upper diagram of FIG. 4, in addition to measured values 54 in the contamination-free state illustrated in FIG. 3, a measured value 56 in the contaminated state of particle sensor 10 is plotted over time. After the compensation of the temperature dependency of the conductivity of the insulator material, a differential signal 58 for a contamination-free state and a differential signal 60 for a contaminated state are obtained. To illustrate the differences between differential signals 58, 60, in the lower diagram a gradient 61 of differential signal 58 for a contamination-free state and a gradient 62 of differential signal 60 for a contaminated state are plotted over time. In addition, a predefined tolerance band 64 is specified, within which contamination-free gradient 62 ranges, while contaminated gradient 61 is outside tolerance band 64.

Figure 5:
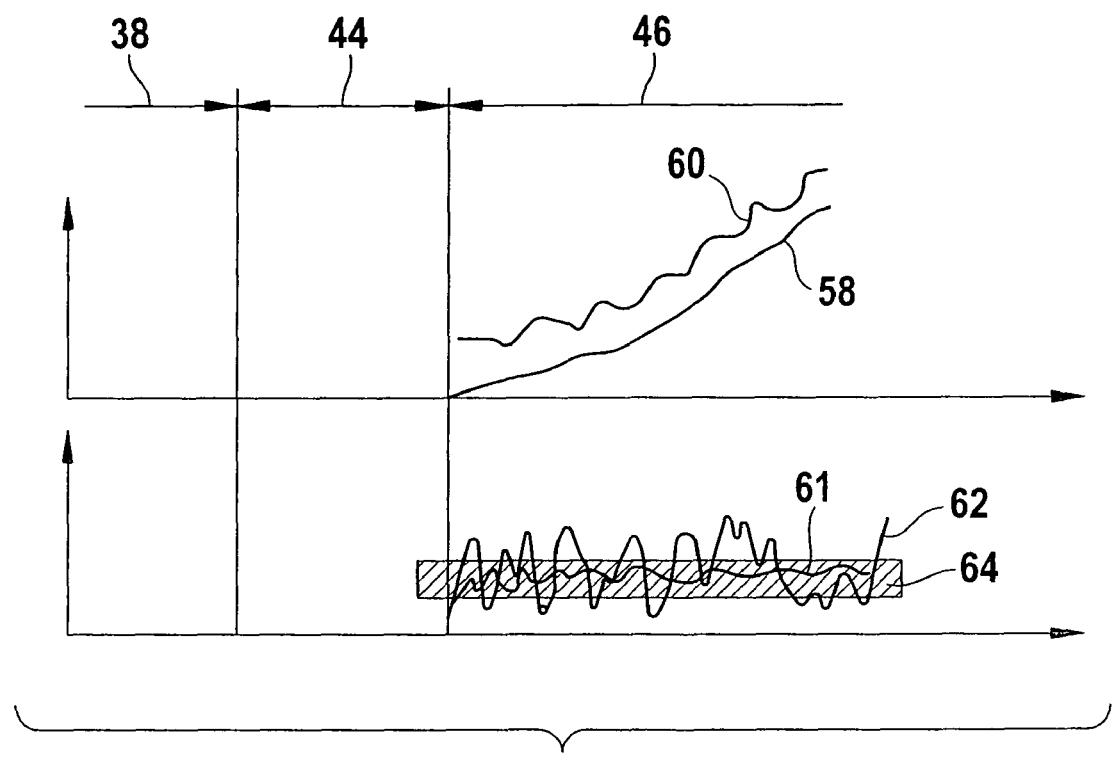
FIG. 5 shows a schematic comparison of parameters obtainable during a modulation in the contaminated and uncontaminated states of the particle sensor in a second time period.

In comparison to FIG. 3 and FIG. 4, the upper diagram in FIG. 5 illustrates the curve of differential signals 58, 60 when the modulation is carried out in linear measuring period 46. For gradients 61, 62 of differential signals 58, 60 illustrated in the lower diagram, the temperature dependency of the soot has also been compensated, resulting in a curve which essentially corresponds to that illustrated in the lower diagram of FIG. 4, in which compensation of the temperature dependency of the soot was not necessary since no electrical signal is generated by the soot during blind period 38. It is apparent in particular that after the compensation step, gradient 62 is clearly outside tolerance band 64 due to current changes in measuring signal 56 caused by shunts, for example because of the presence of ash particles 18 or water. The comparison of the lower diagram in FIG. 5 with the lower diagram in FIG. 4 shows that this is also the case when the temperature dependency of the soot is additionally compensated, since in this case measuring signal 56 obtained as the result of shunts is overcompensated, and gradient 62 is likewise clearly outside tolerance band 64.

What is claimed is:

1. A method for detecting a level of contamination of a particle sensor, comprising:
providing a particle sensor having two electrodes situated on an insulator material for generating an electrical field;
heating the insulator material to above a predetermined limiting temperature, wherein the insulator material begins to become conductive starting at the predefined limiting temperature;
modulating the temperature of the insulator material by at least one of heating and cooling the insulator material between a lower temperature and an upper temperature of a modulation range, wherein both the lower temperature and the upper temperature of the modulation range are above the predetermined limiting temperature;
measuring a variation over time of a measuring signal detected between the electrodes during the modulation;
compensating the measured variation over time of the measuring signal using a theoretical variation over time of the measuring signal in a contamination-free state of the particle sensor, taking a temperature-dependent conductivity of the insulator material into account, in order to obtain a variation over time of a differential signal; and
evaluating the differential signal for determining the level of contamination of the particle sensor.

2. The method as recited in claim 1, wherein the modulation is carried out within a time range in which at least one of substantially constant and substantially linear measuring signal is expected during operation of the particle sensor in the absence of modulation.

3. The method as recited in claim 2, wherein the modulation is carried out before a regeneration period for the particle sensor and within a time range in which the measuring signal changes linearly.

4. The method as recited in claim 2, wherein during the compensating of the measured variation over time of the measuring signal, a further compensation is carried out taking into account a temperature-dependent conductivity of at least one of accumulated ash and accumulated soot particles, and wherein the further compensation is taken into account in the evaluation of the differential signal generated.

5. The method as recited in claim 2, wherein a predefined tolerance band for the differential signal is specified in the evaluation, and wherein a value of the differential signal lying outside the tolerance band results in at least one of a diagnosis of contamination of the particle sensor and a correction of the detected measuring signal, the magnitude of the correction being such that after the correction the differential signal is within the tolerance band.

6. The method as recited in claim 2, wherein during the compensation it is assumed that the change in the temperature-dependent conductivity is substantially linear.

7. The method as recited in claim 2, wherein the heating period is longer than the cooling period during the modulation.

8. The method as recited in claim 2, wherein at least one of the lower temperature and the upper temperature of the modulation range changes during the modulation.

9. The method as recited in claim 1, wherein the modulation is carried out after a regeneration period for the particle sensor and before the measurement of a variation over time of the measuring signal.

10. A particle sensor, comprising:
two electrodes situated on an insulator material for generating an electrical field;
a measuring device for detecting a measuring signal between the electrodes;
a heating apparatus;
a control unit operationally connected to the heating apparatus and configured to heat the insulator material to above a predetermined limiting temperature, wherein the insulator material begins to become conductive starting at the predefined limiting temperature, and also configured to modulate the temperature of the insulator material between a lower temperature and an upper temperature of a modulation range, wherein both the lower temperature and the upper temperature of the modulation range are above the predetermined limiting temperature; and a computing unit configured to (1) compensate a measured variation over time of a measuring signal using a theoretical variation over time of the measuring signal in a contamination-free state of the particle sensor, taking a temperature-dependent conductivity of the insulator material into account, in order to obtain a variation over time of a differential signal, and (2) determine a level of contamination of the particle sensor based on an evaluation of the differential signal in the computing unit.

* * * * *